United States Patent [19]  [11] 4,092,410
Ogata et al.  [45] May 30, 1978

[54] STABILIZATION OF PYRIDO[3,2-a]PHENOXAZINE COMPOUNDS

[75] Inventors: Kazumi Ogata, Toyonaka; Shuzo Iwata, Kobe, both of Japan

[73] Assignee: Senju Pharmaceutical Co., Ltd., Osaka, Japan

[21] Appl. No.: 746,717

[22] Filed: Dec. 2, 1976

[30] Foreign Application Priority Data

Dec. 5, 1975 Japan .................. 50-145450

[51] Int. Cl.² .......... A01N 9/00; A01N 9/22; C07D 265/00; C07D 273/00
[52] U.S. Cl. .................. 424/78; 424/80; 424/175; 424/248.53; 424/248.58; 424/280; 544/99
[58] Field of Search ............ 424/175, 280, 248.53, 424/248.58, 78, 80; 260/244

[56] References Cited

U.S. PATENT DOCUMENTS

| | | | |
|---|---|---|---|
| 2,719,812 | 10/1955 | Hanus | 424/175 |
| 3,132,993 | 5/1964 | Granatek | 424/175 |
| 3,169,092 | 2/1965 | Petraglia et al. | 424/175 |
| 3,429,967 | 2/1969 | DeLuca et al. | 424/175 |
| 3,526,698 | 9/1970 | Polli et al. | 424/175 |
| 3,734,742 | 5/1973 | Morse et al. | 424/280 |
| 3,777,019 | 12/1973 | Levin | 424/175 |
| 3,808,317 | 4/1974 | Hecht et al. | 424/280 |

OTHER PUBLICATIONS

Chem. Abst. 77, 160,177m (1972) Morikawa.
Chem. Abst. 55, 21,494(e) (1961).
Chem. Abst. 54, 11058(h) (1960).

*Primary Examiner*—Albert T. Meyers
*Assistant Examiner*—D. W. Robinson
*Attorney, Agent, or Firm*—Armstrong, Nikaido, Marmelstein & Kubovcik

[57] ABSTRACT

Stabilized solutions of 1-hydroxy-5-oxo-5H-pyrido-[3,2-a]-phenoxazine-3-carboxylic acid (I) and of 1,5-dihydroxypyrido-[3,2-a]phenoxazine-3-carboxylic acid (II) are provided. The solutions contain a stabilizer selected from the group consisting of ascorbic acid, isoascorbic acid and water-soluble salts thereof. The solutions optionally contain an auxiliary stabilizer selected from the group consisting of sodium sulfite, sodium metasulfite and N-acetyl-L-cysteine and may also contain a solubilizer.

6 Claims, No Drawings

STABILIZATION OF PYRIDO[3,2-a] PHENOXAZINE COMPOUNDS

The present invention relates, in one aspect, to a method for stabilizing 1-hydroxy-5-oxo-5H-pyrido[3,2-a]-phenoxazine-3-carboxylic acid (I) and 1,5-dihydroxypyrido-[3,2-a]phenoxazine-3-carboxylic acid (II) which compounds are occurring in a tautomeric relation in solution as represented by the following formula and, in another aspect, to the solution thus stabilized.

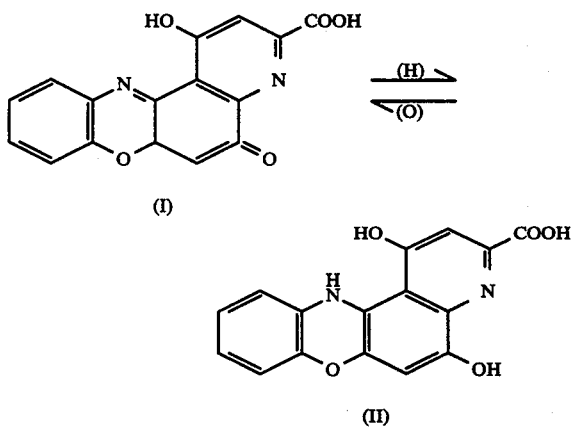

The compound (I) and the compound (II) which is the reduced form thereof are both compounds known per se and obtainable by way of a thermal condensation of O-aminophenol with 4,6-dihydroxyquinoline-5,8-quinone-2-carboxylic acid in acetic acid and in the presence of hydrogen streams.

The compounds (I) and (II) are ready to be transformed into each other. Thus, for example, as sulfurous acid gas is passed through an aqueous solution of compound (I), the latter is reduced to the compound (II), whereas compound (I) is formed as an aqueous solution of compound (II) is allowed to stand in the air.

Compounds (I) and (II) have the property to arrest a progress of cataract and are valuable compounds which have been employed as drugs in many countries including Japan, Greece, Spain, Portugal, Mexico, Brasil, Argentine, Australia, Taiwan and Korea. Because neither of these compounds is readily soluble in water, it is either generally used in the form of an alkali salt or previously dissolved in water with the aid of a base and used as an aqueous solution. Whether in the form of such an aqueous solution or as dissolved in an organic solvent, the compounds are unstable and ready to decompose. This decomposition is considerably accelerated by heat or light and the compounds (I) and (II) have never been successfully kept in solution over an adequate period of time.

The present inventors discovered that if a certain amount of ascorbic acid or isoascorbic acid or a salt of either of them is allowed to be present in a solution containing said compound (I) and/or compound (II), both compounds (I) and (II) remain stable in the solution at pH levels below about 7.

It has further been discovered that the effective amount of said ascorbic acid, isoascorbic acid or salt thereof may be reduced without detracting from the contemplated stabilizing effect by allowing, as an auxiliary stabilizer, one or more members of the class consisting of water-soluble sulfites, metabisulfites and cysteines, to be additionally present in said solution.

It should be understood that when said auxiliary stabilizer, e.g. a sulfite or metasulfite, alone is employed, that is to say in the absence of ascorbic acid or isoascorbic acid or a salt of either of them, the auxiliary stabilizer itself reacts chemically with compounds (I) and (II) and, thereby, makes it impossible to accomplish the object of the invention. Butylated hydroxyanisole (BHA), butylated hydroxytoluene (BHT) and other compounds which are known to be antioxidants for food do not produce the stabilizing effect contemplated and accomplished by the present invention. It is, therefore, considered that ascorbic acid or isoascorbic acid or a salt of either of them has a quite specific action insofar as the field of utility envisaged by the present invention is concerned.

The solubility of compound of formula (I) or (II) is not high, being less than about 0.1 weight percent relative to water. Therefore, in stabilizing compound (I) or/and (II) according to the present invention, ascorbic acid, isoascorbic acid or/and a salt thereof as said stabilizer is used in proportion of 0.01 to 20 weight percent based on the volume of the contemplated final solution (W/V %) in terms of final concentration. It is usually not necessary to employ more than 2 W/V percent of the stabilizer, the preferred range being 0.05 to 1 W/V percent (where W/V % means the number of grams of solute in 100 cm$^3$ of solution).

The aforementioned salt of ascorbic acid or isoascorbic acid may be any salt that is soluble in the particular solvent up to a concentration threshold ensuring the contemplated stabilizing effect, although an alkali metal salt, particularly the sodium salt of ascorbic acid or isoascorbic acid, is advantageous for all practical purposes. Any of such salts may be used in an amount that will give a concentration within the range specified above as the free acid, said amount being easily determinable by a simple stoichiometrical computation.

Where a sulfite, metasulfite or cysteine is employed as said auxiliary stabilizer, it may be employed in a proportion of 0.01 to 1 W/V percent and, preferably, within the range of 0.05 to 0.5 W/V percent. The cation may normally be an alkali metal or ammonium, the sodium salt, e.g. sodium sulfite or metasulfite, being particularly advantageous. Said cysteine means not only cysteine as such but also, for example, N-acylated cysteine such as N-acetyl-L-cysteine. By using such an auxiliary stabilizer, the amount of said ascorbic acid, isoascorbic acid or/and salt may be reduced by 20 to 50 percent.

It should be noted that even the stabilized solution according to the present invention becomes somewhat unstable as its pH is increased beyond pH 7 and, where the solution is used for medicinal purposes, it is desirably controlled at a pH not less than pH 3 for all practical purposes. Thus, when the pH has dropped to less than pH 3, it is desirably readjusted to a level within the aforementioned effective range of pH 3 to 7 by the addition of a suitable alkaline agent such as sodium carbonate, sodium hydroxide or sodium borate. Where the pH is over 7, it may be brought down to a level within said range by means of an appropriate acid such as hydrochloric acid, sulfuric acid, acetic acid or citric acid.

The present invention is also applicable to solutions of compound (I) or/and compound (II) in solvents other than water or in mixtures of such solvents with water, for example propylene glycol, glycerin, sorbitol or any appropriate surfactant or mixtures thereof with water.

Since compounds (I) and (II) tend to precipitate as the concentrations of electrolites or salts in such solutions are elevated, it is possible to add, for the purpose of preventing such precipitation, polyvinyl pyrrolidone, polyvinyl alcohol, procaine hydrochloride or a nonionic surfactant with a HLB number of 11.5 or higher, e.g. Polysorbate 80. The solubilizer is normally employed in an amount within the range of 0.1 to 2 W/V percent, although the optinum amount depends upon its entity and other conditions.

The method of the present invention has a beneficial effect in that it stabilizes a solution of compound (I) and/or compound (II) to an exceptionally satisfactory degree. For example, compared with a solution of said compound or compounds which does not contain any of ascorbic acid, isoascorbic acid and their salts, the stabilized solution according to the present invention is significantly more stable, the percent residue of said compounds (I) and (II) after 5 hours' exposure to direct sunlight or heating under accelerated aging test conditions being more than 50 times higher and, in certain instances, equal to 100 percent.

The following examples and experiments are intended to describe the present invention in further detail.

In each of these experiments, the stabilized solution was put in a colorless ampoule of 20 ml. capacity and, after the ampoule was sealed by fusing, it was subjected to an accelerated aging test which comprised either exposing the ampoule to direct sunlight or heating the ampoule on a water both, for 5 hours in both cases. The result was expressed in the percentage of residual compounds (I) and (II).

Experiment 1

| | |
|---|---|
| 1-Hydroxy-5-oxo-5H-pyrido[3,2-a]-phenoxazine-3-carboxylic acid (sodium salt) | 5.7 mg |
| L-ascorbic acid (or isoascorbic acid) | 0.01 – 20 g |
| Polyvinyl pyrrolidone | 0.2 g |

The above ingredients were added to sterile pure water and the solution was adjusted to pH 5.5 with sodium borate and diluted to make 100 ml.

Table 1

| | | Percent residue after accelerated aging | |
|---|---|---|---|
| Stabilizer | Conc., W/V % | Direct sunlight (5 hrs.) | Heating (5 hrs.) |
| Isoascorbic acid | 0.5 | 100 % | 100 % |
| L-ascorbic acid | 20 | 100 % | 100 % |
| L-ascorbic acid | 2 | 100 % | 100 % |
| L-ascorbic acid | 1 | 100 % | 100 % |
| L-ascorbic acid | 0.5 | 100 % | 100 % |
| L-ascorbic acid | 0.1 | 100 % | 100 % |
| L-ascorbic acid | 0.05 | 89 % | 80 % |
| L-ascorbic acid | 0.01 | 25 % | 24 % |
| Control (not added) | 0 | 2 % | 0 % |

Thus, compared with the control runs free of isoascorbic acid or ascorbic acid in the above accelerated aging tests, 1-hydroxy-5-oxo-5Hpyrido[3,2-a]phenoxazine-3-carboxylic acid (sodium salt) was considerably more stable in the runs carried out in the presence of 0.01% or more of isoascorbic acid or ascorbic acid.

Experiment 2

| | |
|---|---|
| 1-Hydroxy-5-oxo-5H-pyrido[3,2-a]-phenoxazine-3-carboxylic acid (sodium salt) | 5.7 mg |
| L-ascorbic acid (or isoascorbic acid) | 0.05 mg |
| Polyvinyl pyrrolidone | 0.2 g |
| Auxiliary stabilizer (See Table 2) | 0.01 – 1.0 g |

The above ingredients were added to sterile pure water and the solution was adjusted to pH 5.5 with sodium borate and diluted to make 100 ml.

Table 2

| | | Percent residue after accelerated aging | |
|---|---|---|---|
| Auxiliary stabilizer | Conc., W/V % | Direct sunlight (5 hrs.) | Heating (5 hrs.) |
| Sodium hydrogen sulfite | 1.0 | 100 % | 100 % |
| Sodium hydrogen sulfite | 0.1 | 100 % | 100 % |
| Sodium hydrogen sulfite | 0.05 | 100 % | 100 % |
| Sodium hydrogen sulfite | 0.01 | 92 % | 85 % |
| Sodium metabisulfite | 1.0 | 100 % | 100 % |
| N-acetylcysteine | 1.0 | 100 % | 100 % |
| Control (not added) | 0 | 89 % | 80 % |

It will be apparent from Table 2 that in the stabilization of 1-hydroxy-5-oxopyrido[3,2-a]phenoxazine-3-carboxylic acid, the combined use of L-ascorbic acid and an auxiliary stabilizer, such as sodium hydrogen sulfite, gives a superior stabilizing effect as compared with the use of L-ascorbic acid alone.

Experiment 3

| | |
|---|---|
| 1-Hydroxy-5-oxo-5H-pyrido[3,2-a]-phenoxazine-3-carboxylic acid (sodium salt) | 5.7 mg |
| L-ascorbic acid (or isoascorbic acid), 30 % aqueous solution | 1 ml |

The above ingredients were dissolved in about 90 ml of each of various solvents and, after each solution was adjusted to pH 5.5 with a 1N-aqueous solution of sodium hydroxide, it was made up to 100 ml using the corresponding solvent.

Table 3

| | Percent residue after accelerated aging | |
|---|---|---|
| Solvent | Direct sunlight (5 hrs.) | Heating (5 hrs.) |
| Propylene glycol | 100 % | 100 % |
| Propylene glycol, 30% Aq. sol. | 100 % | 100 % |
| Glycerin | 100 % | 100 % |
| Glycerine, 50% Aq. sol. | 100 % | 100 % |
| Sorbitol, 70% Aq. sol. | 100 % | 100 % |
| Sorbitol, 50% Aq. sol. | 100 % | 100 % |
| Polysolbate 80, 35% Aq. sol. | 100 % | 100 % |

It will be seen from Table 3 that there also are obtained solutions of 1-hydroxy-5-oxo-5H-pyrido[3,2-a]phenoxazine-3-carboxylic acid (sodium salt) which are stable under the accelerated aging test conditions described above when said acid is dissolved in solvents, e.g. propylene glycol, 30 (V/V) % aqueous propylene glycol, glycerin, 50 (V/V) % aqueous glycerin, 70 (W/V) % aqueous sorbitol, 50 (W/V) % aqueous sorbitol, or 80% aqueous Polysorbate 80, in the concomitant presence of ascorbic acid or isoascorbic acid.

EXAMPLE 1

Under heating, 26 mg of methyl p-hydroxybenzoate and 14 mg of propyl p-hydroxybenzoate were dissolved in about 80 ml of sterile pure water and, after cooling, 0.3 g. of disodium hydrogen phosphate (12 H$_2$O) and 5.0 mg of 1-hydroxy-5-oxo-5H-pyrido[3,2-a]phenoxazine-3-carboxylic acid were further dissolved. This is followed by the addition of 0.1 g. of isoascorbic acid, 0.2 g. of polyvinyl pyrrolidone and 50 mg. of sodium hydrogen sulfite in the order mentioned. The mixture was adjusted to pH about 5.3 with a sufficient amount of sodium carbonate and, following the addition of 0.8 g. of sodium chloride, it was made up to 100 ml. with sterile pure water. The mixture was aseptically filtered and kept in a sealed glass container.

EXAMPLE 2

Under heating, 26 mg. of methyl p-hydroxybenzoate and 14 mg. of propyl p-hydroxybenzoate were dissolved in about 80 ml. of sterile pure water and, after cooling, 5.0 mg. of 1,5-dihydroxypyrido[3,2-a]phenoxazine-3-carboxylic acid and 0.3 g. of disodium hydrogen phosphate (12 H$_2$O) were dissolved. This was followed by the addition of 0.1 g. of L-ascorbic acid, 0.2 g. of polyvinyl pyrrolidone and 50 mg. of sodium hydrogen bisulfite. The mixture was adjusted to pH 5.3 with a sufficient amount of sodium carbonate. Following the addition of 0.8 g. of sodium chloride, the mixture was made up to 100 ml. with sterile pure water. The solution was aseptically filtered and kept in a sealed glass container.

EXAMPLE 3

Under heating, 26 mg of methyl p-hydroxybenzoate, 14 mg. of propyl p-hydroxybenzoate and 0.5 g. of polyvinyl alcohol were dissolved in about 80 ml. of sterile pure water. After cooling, 5.7 mg. of sodium 1-hydroxy-5-oxo-5H-pyrido[3,2-a]phenoxazine-3-carboxylate was dissolved, followed by addition of 0.1 g. of L-ascorbic acid and 0.9 g. of sodium chloride. The solution was made up to 100 ml. with sterile pure water. The pH of this dilution was about 3.6. The solution was aseptically filtered and kept in a sealed glass container.

EXAMPLE 4

Under heating, 26 mg. of methyl p-hydroxybenzoate, 14 mg. of propyl p-hydroxybenzoate and 0.5 g. of polyvinyl alcohol were dissolved in about 80 ml. of sterile pure water and, after cooling, 0.3 g. of disodium hydrogen phosphate (12 H$_2$O) and 15 mg. of 1-hydroxy-5-oxo-5H-pyrido-[3,2-a]phenoxazine-3-carboxylic acid were added and dissolved. This was followed by the addition of 0.3 g. of L-ascorbic acid, 0.2 g. of polyvinyl pyrrolidone and 2.3 g. of sodium gluconate. The mixture was adjusted to pH 5.5 with a sufficient amount of sodium carbonate and diluted to 100 ml. with sterile pure water. The solution was aseptically filtered and kept in a sealed glass container.

EXAMPLE 5

In about 80 ml. of propylene glycol was dissolved 6 mg. of sodium 1-hydroxy-5-oxo-5H-pyrido[3,2-a]phenoxazine-3-carboxylate, together with 26 mg. of methyl p-hydroxybenzoate and 14 mg. of propyl p-hydroxybenzoate. The solution was mixed with 1 ml. of a 30 (W/V) % aqueous solution of isoascorbic acid. The mixture was adjusted to pH 5.6 with a 1N-aqueous solution of sodium hydroxide and made up to 100 ml. with propylene glycol. The solution was aseptically filtered and kept in a sealed glass container.

EXAMPLE 6

In about 80 ml. of a 70 (W/V) % aqueous solution of sorbitol was dissolved 5.7 mg. of sodium 1-hydroxy-5-oxo-5H-pyrido[3,2-a]phenoxazine-3-carboxylate together with 26 mg. of methyl p-hydroxybenzoate and 14 mg. of propyl p-hydroxybenzoate, followed by the addition of 0.3 g. of L-ascorbic acid. The solution was adjusted to pH 5.5 with a 1N-aqueous solution of sodium hydroxide, aseptically filtered and stored in a sealed glass container.

EXAMPLE 7

Under heating, 26 mg. of methyl p-hydroxybenzoate and 14 mg. of propyl p-hydroxybenzoate were dissolved in about 80 ml. of distilled water. After cooling, 0.1 g. of chlorobutanol, 0.1 g. of sodium hydrogen phosphate (12 H$_2$O), 5 mg. of 1-hydroxy-5-oxo-5H-pyrido[3,2-a]phenoxazine-3-carboxylic acid, 0.2 g. of polyvinyl pyrrolidone, 0.2 g. of L-ascorbic acid, 0.05 g. of sodium hydrogen sulfite, 0.5 g. of monosodium L-glutamate and 0.7 g. of sodium chloride were dissolved in the order mentioned. The mixture was adjusted to pH 5.6 with sodium carbonate and diluted to 100 ml. with distilled water. The solution was filtered and stored in a sealed glass container.

EXAMPLE 8

Under heating, 26 mg. of methyl p-hydroxybenzoate and 14 mg. of propyl p-hydroxybenzoate were dissolved in about 80 ml. of distilled water. After cooling, 0.1 g. of chlorobutanol, 0.1 g. of sodium hydrogen phosphate (12 H$_2$O), 5.7 mg. of sodium 1-hydroxy-5-oxo-5H-pyrido[3,2-a]phenoxazine-3-carboxylate, 0.2 g. of polyvinyl pyrrolidone, 0.3 g. of isoascorbic acid, 0.2 g. of sodium acetate and 0.7 g. of sodium chloride were added and dissolved in the order mentioned. The solution was adjusted to pH 5.6 with sodium carbonate and made up to 100 ml. with distilled water. This solution was filtered and stored in a sealed glass container.

EXAMPLE 9

Under heating, 26 mg. of methyl p-hydroxybenzoate and 14 mg. of propyl p-hydroxybenzoate were dissolved in about 80 ml. of distilled water and, after cooling, 0.1 g. of chlorobutanol, 0.3 g. of disodium hydrogen phosphate, 5 mg. of 1,5-dihydroxypyrido[3,2-a]phenoxazine-3-carboxylic acid, 0.2 g. of polyvinyl pyrrolidone, 0.2 g. of sodium L-ascorbate, 0.8 g. of sodium chloride and 0.1 g. of N-acetylcysteine were added and dissolved in the order mentioned. The solution was adjusted to pH 5.6 with sodium carbonate and diluted to 100 ml. with distilled water. The solution was filtered and stored in a sealed glass container.

EXAMPLE 10

Under heating, 26 mg. of methyl p-hydroxybenzoate and 14 mg. of propyl p-hydroxybenzoate were dissolved in about 80 ml. of distilled water and, after cooling, 0.1 g. of chlorobutanol, 1.0 g. of boric acid, 20 mg. of sodium 1-hydroxy-5-oxo-5H-pyrido[3,2-a]phenoxazine-3-carboxylate, 0.3 g. of polyvinyl pyrrolidone, 0.3 g. of L-ascorbic acid, 0.5 g. of sodium L-glutamate and 0.3 g. of sodium chloride were added in the order mentioned. The solution was adjusted to pH 5.6 with sodium carbonate and diluted with distilled water to make 100 ml. The solution was filtered and stored in a sealed glass container.

EXAMPLE 11

Under heating, 26 mg. of methyl p-hydroxybenzoate and 14 mg. of propyl p-hydroxybenzoate were dissolved in about 80 ml. of distilled water and, after cooling, 0.3 g. of disodium hydrogen phosphate (12 H₂O), 2 mg. of 1,5-dihydroxypyrido[3,2-a]phenoxazine-3-carboxylic acid, 0.4 g. of Polysorbate 80, 0.8 g. of sodium chloride and 0.3 g. of isoascorbic acid were added and dissolved in the order mentioned. The solution was adjusted to pH 5.3 with sodium carbonate and diluted with distilled water to make 100 ml. The solution was filtered and kept in a sealed glass container.

EXAMPLE 12

In about 1,000 ml. of sterile distilled water was dissolved 0.1 g. of sodium 1-hydroxy-5-oxo-5H-pyrido[3,2-a]phenoxazine-3-carboxylate together with 5 g. of procaine hydrochloride. Following the addition of 4 g. of L-ascorbic acid and 50 g. of glucose, the solution was adjusted to pH 5.7 with a 10% aqueous solution of sodium hydroxide. The solution was diluted to 1000 ml., aseptically filtered and distributed into 2 ml.-colorless ampoules.

In any of the above examples, by virtue of the presence of ascorbic acid or isoascorbic acid, 1-hydroxy-5-oxo-5H-pyrido[3,2-a]phenoxazine-3-carboxylic acid or/and its reduced form remained stable, showing a percent residue figure not less than 95 percent even after 3 months standing in an incubator at 40° C. In contrast, in the absence of L-ascorbic acid, isoascorbic acid or salts thereof, the residue of 1-hydroxy-5-oxo-5H-pyrido[3,2-a]phenoxazine-3-carboxylic acid or its reduced form was 0% in all the instances.

What we claim is:

1. A stabilized solution comprising an anti-cataract effective amount of a pyrido[3,2-a]phenoxazine compound of the formula:

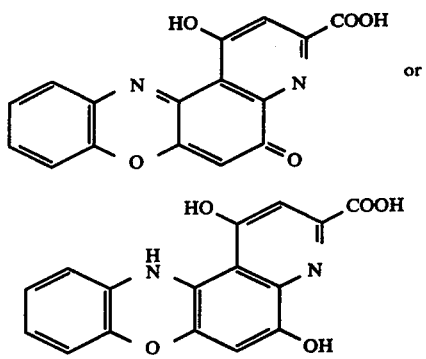

and a stabilizer selected from the group consisting of ascorbic acid, isoascorbic acid and water-soluble salts thereof, wherein the concentration of the stabilizer in the solution is 0.01 to 20 W/V %, and the pH of the solution is 3 to 7.

2. A stabilized solution as claimed in claim 1 further containing an auxiliary stabilizer selected from the group consisting of sodium sulfite, sodium metabisulfite and N-acetyl-L-cysteine, the concentration of the auxiliary stabilizer in the solution being 0.01 to 1 W/V %.

3. A stabilized solution as claimed in claim 1 further containing a solubilizer selected from the group consisting of polyvinyl pyrrolidone, polyvinyl alcohol, procaine hydrochloride and nonionic surfactants with a HLB number not lower than 11.5 the concentration of the solubilizer in the solution being 0.1 to 2 W/V %.

4. A stabilized solution as claimed in claim 1 wherein the medium for the solution is selected from the group consisting of water, propylene glycol, glycerine, sorbitol, mixtures thereof with water and aqueous solutions of surfactants.

5. A stabilized solution as claimed in claim 1 wherein the concentration of the stabilizer in the solution is 0.05 to 1 W/V %.

6. A stabilized solution as claimed in claim 2 wherein the concentration of the auxiliary stabilizer in the solution is 0.05 to 0.5 W/V %.

* * * * *